(12) United States Patent
Gray et al.

(10) Patent No.: US 8,979,825 B2
(45) Date of Patent: Mar. 17, 2015

(54) IMPLANTABLE FLUID DELIVERY DEVICE INCLUDING GAS CHAMBER PRESSURE SENSOR

(75) Inventors: John M. Gray, Brooklyn Park, MN (US); Dale A. Young, Lake Elmo, MN (US)

(73) Assignee: Medtronic, Inc., Minneapolis, MN (US)

( * ) Notice: Subject to any disclaimer, the term of this patent is extended or adjusted under 35 U.S.C. 154(b) by 1006 days.

(21) Appl. No.: 13/087,755

(22) Filed: Apr. 15, 2011

(65) Prior Publication Data

US 2012/0265174 A1    Oct. 18, 2012

(51) Int. Cl.
| | |
|---|---|
| *A61K 9/22* | (2006.01) |
| *A61M 5/142* | (2006.01) |
| *A61M 5/145* | (2006.01) |
| *A61M 5/168* | (2006.01) |

(52) U.S. Cl.
CPC ....... *A61M 5/14276* (2013.01); *A61M 5/14593* (2013.01); *A61M 5/1684* (2013.01); *A61M 2005/14204* (2013.01); *A61M 2205/3331* (2013.01); *A61M 2205/3523* (2013.01)
USPC .................................................. 604/891.1

(58) Field of Classification Search
USPC ............... 604/890.1, 891.1, 505, 65, 67, 131, 604/132, 140, 141, 145, 216
See application file for complete search history.

(56) References Cited

U.S. PATENT DOCUMENTS

| | | |
|---|---|---|
| 4,373,527 A | 2/1983 | Fischell |
| 4,395,259 A | 7/1983 | Prestele et al. |
| 4,486,190 A | 12/1984 | Reinicke |
| 4,561,298 A | 12/1985 | Pond |
| 4,581,018 A | 4/1986 | Jassawalla et al. |
| 4,784,645 A | 11/1988 | Fischell |
| 4,840,064 A | 6/1989 | Fudim |
| 5,006,997 A | 4/1991 | Reich |
| 5,088,983 A | 2/1992 | Burke |
| 5,132,923 A | 7/1992 | Crawford et al. |
| 5,319,964 A | 6/1994 | Stephenson et al. |
| 5,443,450 A * | 8/1995 | Kratoska et al. .............. 604/141 |
| 5,507,737 A | 4/1996 | Palmskog |
| 5,904,666 A | 5/1999 | DeDecker et al. |
| 5,974,873 A | 11/1999 | Nelson |
| 6,152,898 A | 11/2000 | Olsen |
| 6,302,864 B1 | 10/2001 | Nowosielski |
| 6,315,769 B1 | 11/2001 | Peer et al. |

(Continued)

FOREIGN PATENT DOCUMENTS

| | | |
|---|---|---|
| EP | 0622615 A1 | 11/1994 |
| EP | 1649884 A1 | 4/2006 |

(Continued)

OTHER PUBLICATIONS

U.S. Appl. No. 12/762,108, filed Apr. 16, 2010, Kalpin.

(Continued)

*Primary Examiner* — Andrew Gilbert
(74) *Attorney, Agent, or Firm* — Shumaker & Sieffert, P.A.

(57) ABSTRACT

An implantable medical device is configured with a pressure sensor arranged within the device to reliably and accurately measure the pressure within a propellant gas chamber at least partially surrounding a therapeutic fluid reservoir of the device. In one example, a housing of the IMD includes a protrusion that is configured to provide clearance for fluid communication between a propellant gas chamber pressure sensor and the propellant gas chamber.

22 Claims, 6 Drawing Sheets

(56) References Cited

U.S. PATENT DOCUMENTS

| | | | |
|---|---|---|---|
| 6,321,597 B1 | 11/2001 | Demers et al. | |
| 6,458,102 B1 * | 10/2002 | Mann et al. | 604/131 |
| 6,482,177 B1 | 11/2002 | Leinders | |
| 6,537,268 B1 * | 3/2003 | Gibson et al. | 604/891.1 |
| 6,542,350 B1 | 4/2003 | Rogers | |
| 6,542,848 B1 | 4/2003 | Neeser et al. | |
| 6,562,001 B2 * | 5/2003 | Lebel et al. | 604/65 |
| 6,740,059 B2 | 5/2004 | Flaherty | |
| 7,054,782 B2 | 5/2006 | Hartlaub | |
| 7,137,964 B2 | 11/2006 | Flaherty | |
| 7,206,715 B2 | 4/2007 | Vanderveen et al. | |
| 7,255,690 B2 * | 8/2007 | Gray et al. | 604/891.1 |
| 7,481,763 B2 | 1/2009 | Hassler, Jr. et al. | |
| 7,505,869 B2 | 3/2009 | Hartlaub | |
| 7,637,892 B2 * | 12/2009 | Steinbach et al. | 604/153 |
| 7,918,843 B2 * | 4/2011 | Genosar et al. | 604/890.1 |
| 8,206,378 B1 * | 6/2012 | Kalpin et al. | 604/891.1 |
| 8,568,389 B2 * | 10/2013 | Kalpin et al. | 604/891.1 |
| 2002/0087116 A1 | 7/2002 | Hartlaub | |
| 2002/0161328 A1 | 10/2002 | Rogers | |
| 2003/0049135 A1 * | 3/2003 | Gray et al. | 417/44.1 |
| 2004/0249336 A1 | 12/2004 | Faries et al. | |
| 2004/0260233 A1 | 12/2004 | Garibotto et al. | |
| 2005/0075624 A1 * | 4/2005 | Miesel | 604/505 |
| 2005/0187515 A1 | 8/2005 | Varrichio et al. | |
| 2006/0089619 A1 | 4/2006 | Ginggen | |
| 2006/0149220 A1 | 7/2006 | Ullestad et al. | |
| 2006/0270983 A1 * | 11/2006 | Lord et al. | 604/131 |
| 2006/0276744 A1 | 12/2006 | Falk | |
| 2007/0106280 A1 | 5/2007 | Utard et al. | |
| 2007/0239381 A1 | 10/2007 | Ginggen et al. | |
| 2007/0255259 A1 | 11/2007 | Miesel | |
| 2008/0139996 A1 * | 6/2008 | Bowman et al. | 604/67 |
| 2008/0243093 A1 | 10/2008 | Kalpin et al. | |
| 2009/0082757 A1 | 3/2009 | Rogers et al. | |
| 2010/0125246 A1 | 5/2010 | Kalpin | |
| 2010/0137842 A1 | 6/2010 | Gibson | |
| 2011/0296925 A1 * | 12/2011 | Miesel et al. | 73/718 |
| 2012/0265144 A1 * | 10/2012 | Kalpin et al. | 604/140 |

FOREIGN PATENT DOCUMENTS

| | | |
|---|---|---|
| EP | 1839635 A1 | 10/2007 |
| WO | 0072900 A1 | 12/2000 |
| WO | 03068049 A2 | 8/2003 |
| WO | 2007041471 A2 | 4/2007 |
| WO | 2008121421 A1 | 10/2008 |

OTHER PUBLICATIONS

U.S. Appl. No. 12/762,121, filed Apr. 16, 2010, Kalpin.

U.S. Appl. No. 12/762,064, filed Apr. 16, 2010, Nelson Konen et al.

U.S. Appl. No. 13/085,573, filed Apr. 13, 2011, Kalpin et al.

* cited by examiner

IMPLANTABLE FLUID DELIVERY DEVICE INCLUDING GAS CHAMBER PRESSURE SENSOR

BACKGROUND

A variety of medical devices are used for chronic, i.e., long-term, delivery of fluid therapy to patients suffering from a variety of conditions, such as chronic pain, tremor, Parkinson's disease, epilepsy, urinary or fecal incontinence, sexual dysfunction, obesity, spasticity, or gastroparesis. For example, pumps or other fluid delivery devices can be used for chronic delivery of therapeutic fluids, such as drugs to patients. These devices are intended to provide a patient with a therapeutic output to alleviate or assist with a variety of conditions. Typically, such devices are implanted in a patient and provide a therapeutic output under specified conditions on a recurring basis.

One type of implantable fluid delivery device is a drug infusion device that can deliver a drug or other therapeutic fluid to a patient at a selected site. A drug infusion device may be partially or completely implanted at a location in the body of a patient and deliver a fluid medication through a catheter to a selected delivery site in the body. Drug infusion devices, such as implantable drug pumps, commonly include a reservoir for holding a supply of the therapeutic fluid, such as a drug, for delivery to a site in the patient. The fluid reservoir can be self-sealing and accessible through one or more ports. A pump is fluidly coupled to the reservoir for delivering the therapeutic fluid to the patient. A catheter provides a pathway for delivering the therapeutic fluid from the pump to the delivery site in the patient.

SUMMARY

In general, this disclosure describes techniques for arranging a pressure sensor and fluidly connecting the sensor to a propellant gas chamber of an IMD such that the sensor can measure the pressure within the chamber reliably and accurately.

In one example, an implantable fluid delivery device including a reservoir, a housing, and a pressure sensor. The reservoir is configured to store a therapeutic fluid. The housing defines a chamber configured to at least partially surround the reservoir. The chamber is configured to be filled with a propellant gas configured to regulate a pressure within the reservoir. A pressure sensor is configured to sense a pressure within the chamber. The housing comprises a protrusion configured to provide clearance for fluid communication between the pressure sensor and the chamber.

In one example, an implantable fluid delivery device including a housing including two generally circular walls connected by an annular wall defining a chamber configured to at least partially surround a therapeutic fluid reservoir. The chamber is configured to be filled with a propellant gas configured to regulate a pressure within the reservoir. The housing includes a protrusion configured to provide clearance for fluid communication between the chamber and a pressure sensor configured to sense a pressure within the chamber.

In another example, a system includes a reservoir, a housing, and a pressure sensor. The reservoir is configured to store a therapeutic fluid delivered by an implantable fluid delivery device. The housing defines a chamber configured to at least partially surround the reservoir. The pressure sensor is configured to sense a pressure within the chamber. The system also includes means for providing clearance for fluid communication between the pressure sensor and the chamber.

The details of one or more examples disclosed herein are set forth in the accompanying drawings and the description below. Other features, objects, and advantages will be apparent from the description and drawings, and from the claims.

DETAILED DESCRIPTION

Figure 1:
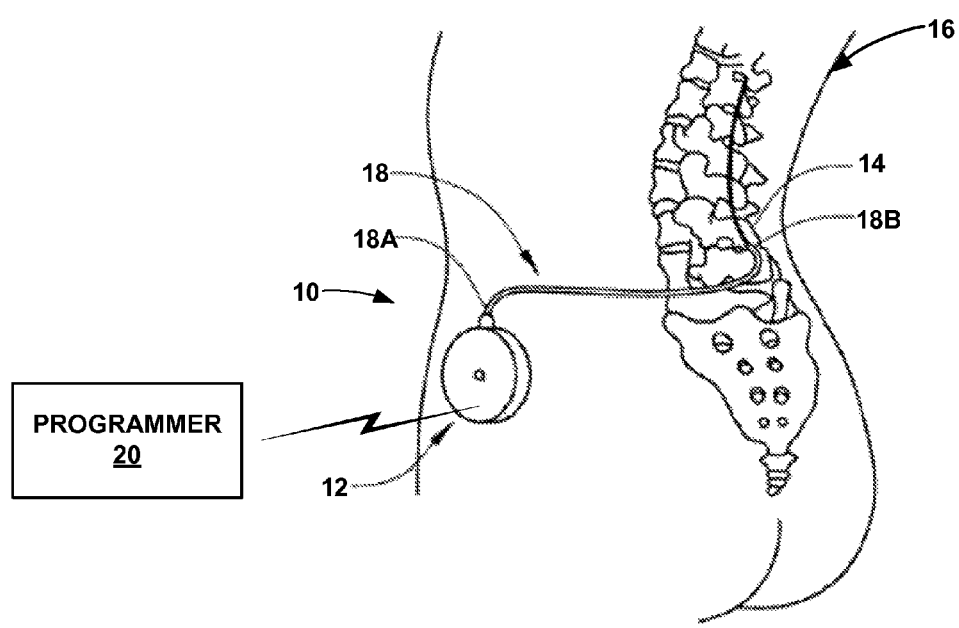
FIG. 1 is a conceptual diagram illustrating an example of a fluid delivery system including an implantable fluid delivery device configured to deliver a therapeutic fluid to a patient via a catheter.

It is generally useful for the safe and intended operation of implantable fluid delivery devices (hereinafter IMD or device) to monitor the volume of therapeutic fluid in the reservoir of the device as the fluid is being delivered to a patient. For example, it is useful to have an actual measurement or an estimate derived from measured values of the volume of therapeutic fluid in the reservoir of an IMD. Fluid volume can be determined by calculating the volume based on an initial fill volume in the reservoir minus the amount of fluid dispensed to the patient over time. However, neither the fill volume nor the amount of fluid dispensed over time in such examples is measured. Instead, the fill volume is commonly specified by a user, e.g. entered via an external programmer, and thus is subject to human error. Additionally, the amount of fluid dispensed over time is a theoretical calculation based on an expected dispense rate or volume programmed into the device, which assumes perfectly consistent operation of the IMD over time, i.e., assumes that the device dispenses fluid at the same rate at all times.

It may also be useful to verify that a clinician has correctly accessed a refill port of an IMD and is actually filling the reservoir with therapeutic fluid to prevent an unintended injection of the fluid into a tissue pocket within a patient. Additionally, it may be useful to monitor the fill status of the reservoir of such devices to detect unexpected changes in the amount of fluid in the device. An unexpected change in fluid volume may occur when a patient or another person, outside of a clinical environment, attempts to access the refill port of the reservoir to remove therapeutic fluid from the device. Another cause of unexpected changes in fluid volume in the reservoir may be valve leakage or pump stroke volume variation. Unexpected changes in reservoir volume may affect the operation of the device by causing underdosing or overdosing of the patient with the therapeutic fluid delivered by the IMD. Underdosing of a patient may be of particular interest in cases where rapidly reducing the amount of therapeutic fluid delivered by the device to the patient may cause withdrawal symptoms. Device awareness of reservoir fill status is important for these and other reasons related to the proper operation of IMDs and the efficacious delivery of therapy to patients by such devices.

Although different mechanisms are capable of determining the volume of therapeutic fluid in the reservoir of an IMD, one convenient and economical method is to employ a pressure sensor that monitors pressure within the device over time. Generally speaking, the volume of the reservoir of an IMD may be extrapolated from a sensed pressure. However, the relationship between sensed pressure and reservoir fluid volume varies with temperature, which may not be constant. For example, in the event the temperature of a therapeutic fluid added to the reservoir of an IMD is not the same as the reservoir temperature, fluid volume will depend both on pressure changes and temperature changes. Therefore, it also may be necessary, in temperature-dependent applications, to determine one or more temperatures related to filling the reservoir of an IMD with a therapeutic fluid. In particular, it may be necessary for the proper monitoring of reservoir volume to determine the temperature of the reservoir of the IMD, which may, in some examples, be equated to the temperature of the gas propellant used to pressurize the reservoir of the device and the temperature of therapeutic fluid added to the reservoir.

One challenge with extrapolating reservoir volume from pressure in temperature-dependent applications is that the temperatures of the reservoir of the IMD and the therapeutic fluid are unknown. Both temperatures may be measured by employing additional sensors, such as temperature sensors to directly measure temperature. However, incorporation of additional sensors may add cost and complexity to the IMD. Measuring temperatures directly may also complicate the process of refilling an IMD with therapeutic fluid, because, e.g., a user, such as a clinician may be required to measure and then enter the fluid temperature into a programmer to be transmitted to the IMD. Finally, even direct temperature measurement may involve analytical complications, as thermodynamic effects on temperature and pressure changes in the IMD must be accounted for with respect to the measurements taken by some temperature sensors employed to measure the temperature of the reservoir and/or the fluid.

In some cases, temperature effects on volume estimation may be substantially removed by employing a measured pressure differential including a measurement of the pressure within a propellant gas chamber surrounding the reservoir of the IMD. Examples of such techniques for estimating the volume of therapeutic fluid in a reservoir of an IMD are described in U.S. patent application Ser. No. 13/085,573, filed Apr. 13, 2011, and entitled "METHOD AND DEVICE FOR ESTIMATING VOLUME OF FLUID IN THERAPEUTIC FLUID DELIVERY DEVICE RESERVOIR," which is incorporated herein in its entirety by this reference. In some current IMD designs, constraints on the clearance between the propellant gas chamber and the fluid reservoir of the IMD may make measuring the pressure within the chamber challenging and ultimately even impractical. Examples according to this disclosure provide techniques for arranging a pressure sensor and fluidly connecting the sensor to a propellant gas chamber of an IMD such that the sensor can measure the pressure within the chamber reliably and accurately.

FIG. 1 is a conceptual diagram illustrating an example of a therapy system 10, which includes implantable medical device (IMD) 12, catheter 18, and external programmer 20. IMD 12 is connected to catheter 18 to deliver at least one therapeutic fluid, e.g. a pharmaceutical agent, pain relieving agent, anti-inflammatory agent, gene therapy agent, or the like, to a target site within patient 16. IMD 12 includes an outer housing that, in some examples, is constructed of a biocompatible material that resists corrosion and degradation from bodily fluids including, e.g., titanium or biologically inert polymers. IMD 12 may be implanted within a subcutaneous pocket relatively close to the therapy delivery site. For example, in the example shown in FIG. 1, IMD 12 is implanted within an abdomen of patient 16. In other examples, IMD 12 may be implanted within other suitable sites within patient 16, which may depend, for example, on the target site within patient 16 for the delivery of the therapeutic fluid. In still other examples, IMD 12 may be external to patient 16 with a percutaneous catheter connected between IMD 12 and the target delivery site within patient 16.

IMD 12 delivers a therapeutic fluid from a reservoir (not shown) to patient 16 through catheter 18 from proximal end 18A coupled to IMD 12 to distal end 18B located proximate to the target site. Example therapeutic fluids that may be delivered by IMD 12 include, e.g., insulin, morphine, hydromorphone, bupivacaine, clonidine, other analgesics, baclofen and other muscle relaxers and antispastic agents, genetic agents, antibiotics, nutritional fluids, hormones or hormonal drugs, gene therapy drugs, anticoagulants, cardiovascular medications or chemotherapeutics.

Catheter 18 can comprise a unitary catheter or a plurality of catheter segments connected together to form an overall catheter length. External programmer 20 is configured to wirelessly communicate with IMD 12 as needed, such as to provide or retrieve therapy information or control aspects of therapy delivery (e.g., modify the therapy parameters such as rate or timing of delivery, turn IMD 12 on or off, and so forth) from IMD 12 to patient 16.

Catheter 18 may be coupled to IMD 12 either directly or with the aid of a catheter extension (not shown in FIG. 1). In the example shown in FIG. 1, catheter 18 traverses from the implant site of IMD 12 to one or more targets proximate to spinal cord 14. Catheter 18 is positioned such that one or more fluid delivery outlets (not shown in FIG. 1) of catheter 18 are proximate to the targets within patient 16. In the example of FIG. 1, IMD 12 delivers a therapeutic fluid through catheter 18 to targets proximate to spinal cord 14.

IMD 12 can be configured for intrathecal drug delivery into the intrathecal space, as well as epidural delivery into the epidural space, both of which surround spinal cord 14. In some examples, multiple catheters may be coupled to IMD 12 to target the same or different nerve or other tissue sites within patient 16, or catheter 18 may include multiple lumens to deliver multiple therapeutic fluids to the patient. Therefore, although the target site shown in FIG. 1 is proximate to spinal cord 14 of patient 16, other applications of therapy system 10 include alternative target delivery sites in addition to or in lieu of the spinal cord of the patient.

Programmer 20 is an external computing device that is configured to communicate with IMD 12 by wireless telemetry. For example, programmer 20 may be a clinician programmer that the clinician uses to communicate with IMD 12 and program therapy delivered by the IMD. Alternatively, programmer 20 may be a patient programmer that allows patient 16 to view and modify therapy parameters associated with therapy programs. The clinician programmer may include additional or alternative programming features than the patient programmer. For example, more complex or sensitive tasks may only be allowed by the clinician programmer to prevent patient 16 from making undesired or unsafe changes to the operation of IMD 12. Programmer 20 may be a handheld or other dedicated computing device, or a larger workstation or a separate application within another multi-function device.

In examples according to this disclosure, IMD 12 includes a pressure sensor configured to measure a pressure within a chamber housing propellant gas employed to equalize pressures in a therapeutic fluid reservoir of the IMD. In one example, IMD 12 may include a reservoir configured to store a therapeutic fluid and a chamber at least partially surrounding the reservoir and configured to be filled with a propellant gas that regulates the pressure within the reservoir. In one example, the propellant gas is employed to maintain a substantially constant pressure within the reservoir in order to deliver the therapeutic fluid to patient 16 consistently and accurately over time. IMD 12 may be configured to control a pressure sensor to measure the pressure within the propellant gas chamber, e.g. in the process of estimating the volume of therapeutic fluid in the reservoir of the IMD. In some examples, IMD 12 may also include additional sensors, including, e.g., a reservoir pressure sensor configured to sense a pressure within the reservoir of the device.

Figure 2:
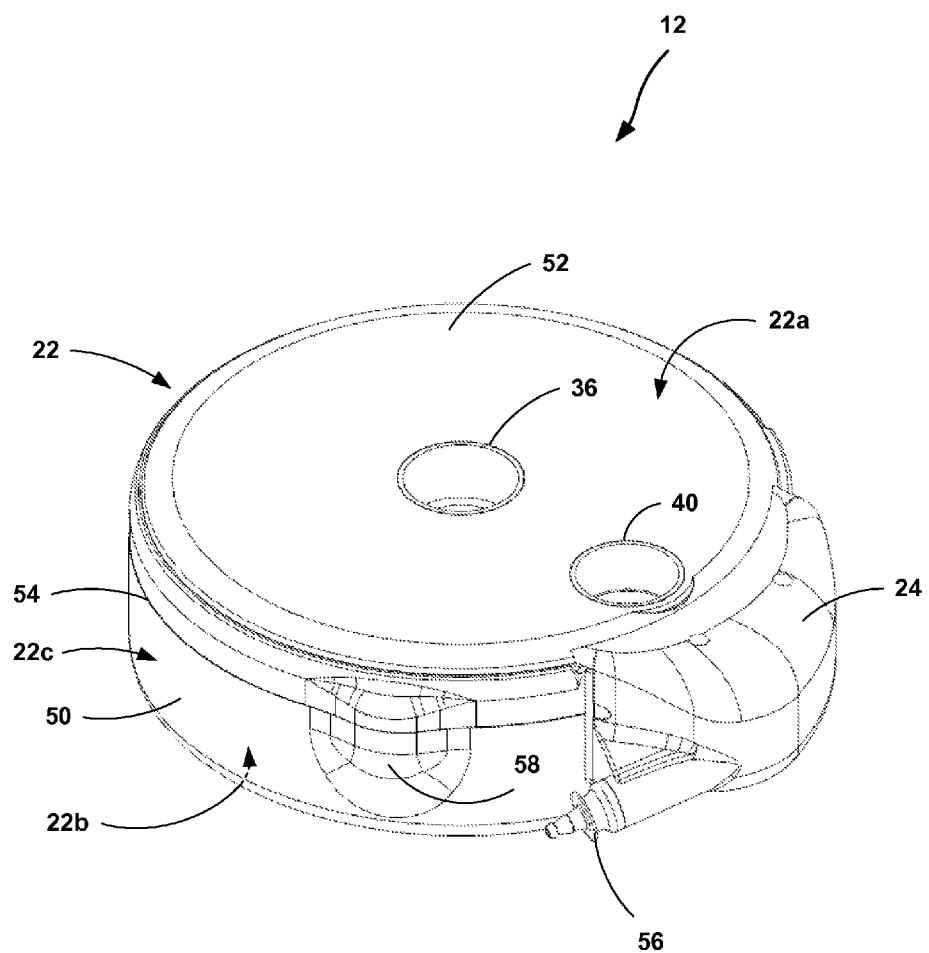
FIG. 2 is a perspective view illustrating an example configuration of the implantable fluid delivery device of FIG. 1.

FIG. 2 is a perspective view illustrating an example configuration of IMD 12 including housing 22, header 24, refill port 36, and catheter access port (CAP) 40. Housing 22 of IMD 12 is generally cylindrical, including two circular walls 22a, 22b (only one of which is visible in the view of FIG. 2) connected to one another by annular wall 22c. Housing 22 is divided into two parts, which include shield 50 and bulkhead 52. Shield 50 and bulkhead 52 of housing 22 are connected at seam 54. In one example, seam 54 includes a weld joint that is configured to create a hermetic seal between shield 50 and bulkhead 52. Housing may be constructed from biocompatible materials that resist corrosion and degradation from bodily fluids including, e.g., titanium or biologically inert polymers. Housing may be fabricated using a variety of known solid material manufacturing techniques, including, e.g. pressing, casting, molding, or any one or more of various material removal processes, including, e.g., milling, turning, grinding, electrical discharge machining (EDM), or laser or torch cutting. For example, shield 50 may be pressed from sheet stock of a metal or metal alloy, e.g. a titanium alloy, while bulkhead 52 is machined from stock piece of a similar or different material. In another example in which part or all of housing 22 is fabricated from a plastic, shield 50 and/or bulkhead 52 may be manufactured using injection molding techniques.

Figure 3A:
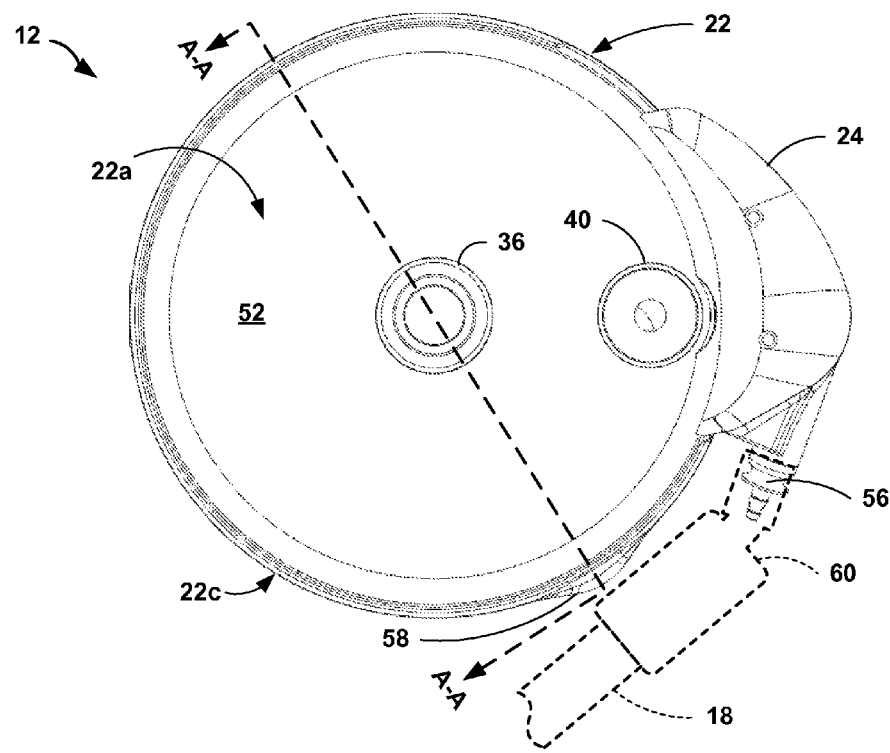
FIG. 3A is a plan view of the example implantable fluid delivery device of FIG. 2.
Figure 3B:
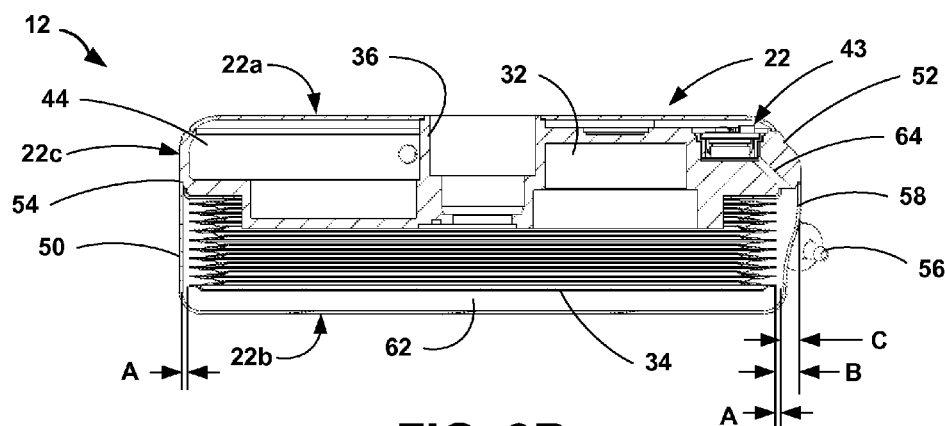
FIGS. 3B and 3C are cross-sectional side views of the example implantable fluid delivery device of FIGS. 2 and 3A cut along the section line A-A of FIG. 3A.

In one example, shield 50 is a thin wall enclosure that receives and surrounds the reservoir of IMD 12 (see FIG. 3B). The space between the inner surfaces of the walls of shield 50 and the reservoir of IMD 12 defines a chamber within which a propellant gas is held at pressure. The propellant gas in the gas chamber within shield 50 is employed to regulate the pressure within the reservoir of IMD 12. Bulkhead 52 houses a number of components of IMD 12 including, e.g., control electronics, e.g. processor(s), memory, and telemetry, as well as the IMD fluid delivery pump, the power source for the IMD, and one or more sensors. One sensor housed by bulkhead 52 of IMD 12 is a gas propellant chamber pressure sensor, which may be employed to measure the pressure of the gas chamber within shield 50 in which the propellant gas is housed. In one example, IMD 12 employs propellant gas chamber pressure measurements to estimate the volume of fluid within the reservoir of the device.

Header 24 includes catheter junction 56 and is connected to housing 22 of IMD 12 generally along a portion of annular side wall 22c. Header 24 forms the connection between IMD 12 and a catheter through which the device delivers a therapeutic fluid to a patient, e.g. catheter 18 of FIG. 1. Tubes and/or passages in header 24 are provide a fluid connection between the outlet of the fluid delivery pump of IMD 12 and catheter junction 56, to which the fluid delivery catheter is either directly connected or indirectly connected via an extension connected to the junction.

As noted above, housing 22 of IMD 12 is generally cylindrical, including two circular walls 22a, 22b connected to one another by annular wall 22c. In the example of FIG. 2, shield 50 includes one of the two generally circular walls 22b of housing 22, and bulkhead 52 includes the other circular wall 22a of housing 22. Shield 50 also includes a portion of annular side wall 22c below seam 54 in the view of FIG. 2, while the remaining portion of annular side wall 22c of housing 22 is part of bulkhead 52, i.e. above seam 54 in the view of FIG. 2. Annular side wall 22c of housing 22 includes protrusion 58. Protrusion 58 in annular side wall 22c may be configured to provide clearance between the reservoir of IMD 12 received within shield 50 and the inner walls of the shield. In other words, protrusion 58 may be configured to provide clearance in the gas propellant chamber within shield 50 and at least partially surrounding the reservoir of IMD 12. The function and configuration of protrusion 58 is described in greater detail with reference to FIGS. 3A and 3B below.

In FIG. 2, refill port 36 of IMD 12 is arranged in bulkhead 52 near the center of circular wall 22a. Refill port 36 is connected to the reservoir of the device. Periodically, fluid may need to be supplied percutaneously to the reservoir of IMD 12 because all of a therapeutic fluid has been or will be delivered to patient 16, or because a clinician wishes to replace an existing fluid with a different fluid or similar fluid with different concentrations of therapeutic ingredients. Refill port 36 can therefore comprise a self-sealing membrane, or septum to prevent loss of therapeutic fluid delivered to the reservoir via refill port 36. For example, after a percutaneous delivery system, e.g., a hypodermic needle, penetrates the membrane of refill port 36, the membrane may seal shut when the needle is removed from refill port 36.

Catheter access port 40 is arranged in bulkhead 52 of IMD 12 near the perimeter of circular wall 22a. Catheter access port 40 is connected to internal tubing and/or channels in bulkhead 52 and from there to a delivery catheter that is connected to IMD 12 via catheter junction 56 of header 24. Clinicians or other users may access a catheter connected to IMD 12 directly via catheter access port 40, e.g., to flush the catheter with saline, deliver a therapeutic fluid directly to the patient via the catheter, or in the process of executing bridging bolus.

FIGS. 3A and 3B illustrate in greater detail features and components of the example configuration of IMD 12 of FIG. 2. FIG. 3A is a plan view of the example configuration of IMD 12 of FIG. 2. In FIG. 3A, IMD 12, including housing 22, bulkhead 52, header 24, refill port 36 and catheter access port 40, is illustrated with a schematic representation of catheter extension 60 and catheter 18 connected to catheter junction 56. Protrusion 58 in annular sidewall 22c of housing 22 may be arranged circumferentially in a number of locations on the periphery of the housing. In the example of FIGS. 2-3B, however, protrusion 58 is adjacent catheter extension 20 and catheter 18 connected to catheter junction 56. Arranging protrusion 58 adjacent catheter junction 56, and, in particular, in unused space between annular side wall 22c of housing 22 of IMD 12 and one of catheter extension 60 and catheter 18, may prevent or reduce the risk that the protrusion will create a new surface feature on the IMD that acts as an irritant to the patient in which the device is implanted and/or a source of tissue damage or infection.

FIG. 3B is a cross-sectional side view of the example configuration of IMD 12 of FIGS. 2 and 3A cut along the section line A-A of FIG. 3A. In FIG. 3B, IMD 12 includes housing 22, bulkhead 52, header 24, and refill port 36, as well as internal components fluid delivery pump 32, reservoir 34, propellant gas chamber pressure sensor 43, and power source 44. During operation of IMD 12, the device controls fluid delivery pump 32 with the aid of instructions associated with program information, e.g. information stored in memory of the device, to deliver a therapeutic fluid to patient 16 via catheter 18. Instructions executed by IMD 12 may, for example, define therapy programs that specify the dose of therapeutic fluid that is delivered to a target tissue site within patient 16 from reservoir 30 via catheter 18. The programs may further specify a schedule of different therapeutic fluid rates and/or other parameters by which IMD 12 delivers therapy to patient 16.

Fluid delivery pump 32 draws fluid from reservoir 34 and pumps the fluid through internal tubing or cavities in bulkhead 52 of housing 22 of IMD 12 to catheter 18 through which the fluid is delivered to patient 16 to effect one or more of the treatments described above, e.g. in accordance with a program stored on memory of the IMD. Fluid delivery pump 32 can be any mechanism that delivers a therapeutic fluid in some metered or other desired flow dosage to the therapy site within patient 16 from reservoir 30 via implanted catheter 18. In one example, fluid delivery pump 32 is a squeeze pump that squeezes internal tubing 38 in a controlled manner, e.g., such as a peristaltic pump, to progressively move fluid from reservoir 34 to the distal end of catheter 18 and then into patient 16 according to parameters specified by the therapy program stored on memory 28 and executed by processor 26. In various examples, fluid delivery pump 32 may be an axial pump, a centrifugal pump, a pusher plate pump, a piston-driven pump, or other means for moving fluid through internal tubing 38 and catheter 18. In one example, fluid delivery pump 32 is an electromechanical pump that delivers fluid by the application of pressure generated by a piston that moves in the presence of a varying magnetic field and that is configured to draw fluid from reservoir 34 and pump the fluid through internal tubing 38 and catheter 18 to patient 16.

As illustrated in FIG. 3B, reservoir 34 includes an expandable and contractible bellows, the pressure of which is maintained via a propellant, e.g. a propellant gas. The propellant gas acts as a pressure-providing means to the chamber of reservoir 34, which regulates the pressure within the reservoir by applying pressure to the flexible bellows structure to discharge the therapeutic fluid stored in the reservoir through internal tubing 38 to fluid delivery pump 32. In one example, the propellant gas is employed to maintain a substantially constant pressure within reservoir 34 in order to deliver the therapeutic fluid through tubing or cavities in bulkhead 52 to pump 32 consistently and accurately over time. The propellant gas is held within chamber 62 surrounding reservoir 34, which is defined by the inner walls of shield 50 of housing 22 of IMD 12. The propellant gas used to regulate the pressure of reservoir 34 of IMD 12 may be a fluid that is in phase change between a liquid state and a gas state when, e.g., in equilibrium between phases at around 35-37 degrees Celsius which is a common temperature range of the body of patient 16. The propellant gas employed in examples of IMD 12 may comprise at least one of butane, perflurohexane, or perfluropentane.

IMD 12 includes gas chamber pressure sensor 43, which is configured to measure pressure in chamber 62. Pressure sensor 43 is arranged in bulkhead 52 adjacent protrusion 58 and is fluidly connected to propellant gas chamber 62 via fluid connection 64. Regardless of where arranged, pressure sensor 43 is communicatively connected to control electronics of IMD 12 to transmit pressure-related information to the electronics, e.g. for analysis and storage on memory of the device in order to, e.g., determine the actual rate at which therapeutic fluid is delivered from reservoir 34 to patient 16, and/or the actual volume of therapeutic fluid remaining in the reservoir.

IMD 12 may include additional sensors, including a reservoir pressure sensor configured to measure pressure in reservoir 34. The reservoir pressure sensor may be arranged in a number of locations within IMD 12 including, e.g., in reservoir 34 or refill port 36. Regardless of where arranged, the reservoir pressure sensor may be communicatively connected to control electronics of IMD 12 to transmit pressure-related information to the electronics, e.g. for analysis and storage on memory of the device in order to, e.g., determine the actual rate at which therapeutic fluid is delivered from reservoir 34 to patient 16, and/or the actual volume of therapeutic fluid remaining in the reservoir.

Gas chamber pressure sensor 43, as well as a reservoir pressure sensor of IMD 12, may be electronically coupled to control electronics of the device, in a variety of ways including electrical wiring (not shown) or a wireless link between the pressure sensor and the electronics. Pressure sensor 43 may each be any device capable of measuring pressure of propellant gas chamber 62 of IMD 12. For example, pressure sensor 43 may be a capacitive measurement device which determines pressure by measuring the change in capacitance of a flexible membrane attached to but insulated from a conductive, gas-filled cavity due to deflections caused by pressure applied over the flexible membrane (i.e., a capacitive pressure sensor). Alternatively, pressure sensor 43 may be a sensor that utilizes the piezo-electric effect (i.e., a piezo-electric pressure sensor) or resistive change due to metallic strain (i.e., a strain gauge pressure sensor) in order to measure pressure applied. Other types of pressure sensors not specifically described may also be employed in examples according to this disclosure.

To reduce size while increasing fluid storage capacity, IMD 12 employs shield 50 of housing 22 that closely envelopes reservoir 34 with relatively little space or clearance left between the reservoir and the inner walls of the shield, i.e. very little space defined by propellant gas chamber 62. In the example of 3B, gas chamber 62 surrounds reservoir 34 such that a periphery of the reservoir is offset from annular side wall 22c by a distance A, which is substantially constant around the circumference of housing 22, except at protrusion 58, as described in greater detail below. The size of the gap between annular side wall 22c and reservoir 34 within gas chamber 62, e.g. distance A in FIG. 3B, may make fabricating a fluid connection between a pressure sensor configured to measure the pressure in the gas chamber challenging or even impractical.

For example, it may not be possible or practical to repeatably and reliably cross-drill a hole or other channel or passage through bulkhead 52 from a location at which a gas chamber pressure sensor may be arranged into propellant gas chamber 62 because of the size of the tool necessary to machine the hole and the tolerances associated with such a process. For example, cross-drilling such a hole may, because of inaccuracies in the process, cause the tool to pierce or otherwise damage reservoir 34 or other adjacent structures within IMD 12. In another example, a hole or other passage is machined into bulkhead 52 before the bulkhead is connected to shield 50 in a final assembly procedure of IMD 12. In such an example, a weld connecting shield 50 to bulkhead 52 at seam 54 applied after the hole is drilled in the bulkhead may occlude the hole where it meets propellant gas chamber 62 such that a pressure sensor placed in the bulkhead at the other end of the hole may not be able to reliably or accurately measure the pressure within the chamber.

In view of the foregoing challenges with measuring the pressure within a propellant gas chamber of an IMD, examples according to this disclosure include IMD housings with a protrusion that is configured to provide clearance for a fluid connection between a propellant gas chamber pressure sensor and the gas chamber to enable the pressure sensor to reliably and accurately measure the pressure within the chamber. In FIG. 3B, housing 22 includes protrusion 58 which acts to create additional clearance within propellant gas chamber 62 at a junction between fluid connection 64 and the gas chamber. Fluid connection 64 in the example of FIG. 3B is a hole or other passage in bulkhead 52. In another example, however, fluid connection may be a tube or other conduit connecting gas chamber pressure sensor 43 and propellant gas chamber 62.

Protrusion 58 is formed in annular side wall 22c of housing 22. In the example of FIG. 3B, protrusion 58 increases the clearance within chamber 62 between reservoir 34 and annular side wall 22c by a distance C from the distance A, which defines the gap around the rest of the circumference of housing 22, to distance B. In one example, the distance defining the clearance within gas chamber 62 provided by protrusion 58 in annular side wall 22c may be sized as a multiple of the distance A in FIG. 3B. In another example, the distance B defining the clearance within gas chamber 62 provided by protrusion 58 in annular side wall 22c may be defined as a function of a size of fluid connection 64 between propellant chamber pressure sensor 43 and gas chamber 62. For example, fluid connection 64 between propellant chamber pressure sensor 43 and gas chamber 62 may include a hole or other channel through bulkhead 52 including a generally circular cross-section. In such an example, the distance B defining the clearance within gas chamber 62 provided by protrusion 58 in annular side wall 22c may be defined as a function of the diameter of fluid connection 64. In another example, the distance defining the clearance within gas chamber 62 provided by protrusion 58 in annular side wall 22c, e.g. distance B in the example of FIG. 3B, may be an absolute value.

Although the periphery of reservoir 34 is illustrated and described with reference to the example of FIG. 3B as the convolutions of the bellows type reservoir of IMD 12, in another example, a different component or portion of reservoir 34 may limit or make impractical fabrication of a fluid connection to a pressure sensor configured to measure the pressure in gas chamber 62. For example, as illustrated in the detail view of FIG. 3C, top flange 35 of reservoir 34 may limit the space within which a cross-drilled hole or other channel or passage may be repeatably and reliably machined through bulkhead 52 from a location at which a gas chamber pressure sensor may be arranged into propellant gas chamber 62. In such an example, protrusion 58 may be formed in annular side wall 22c of housing 22 to increase the distance, D, within chamber 62 between reservoir flange 35 and annular side wall 22c, which defines the gap around the rest of the circumference of housing 22, to a distance that accommodates a passage between the pressure sensor and the chamber. In one example, the limiting distance between reservoir flange 35 and annular side wall 22c, i.e. distance D in FIG. 3C, may be in a range from approximately 0.07 millimeters (0.00275 inches) to approximately 0.29 millimeters (0.0115 inches). In one example according to this disclosure, the distance defining the clearance within gas chamber 62 provided by protrusion 58 in annular side wall 22c may be sized as a multiple of the distance D in FIG. 3C. For example, the distance defining the clearance within gas chamber 62 provided by protrusion 58 in annular side wall 22c may be 9 times larger than the distance D that defines the gap between the wall and reservoir flange 35 around the rest of the circumference of housing 22. In another example, the distance defining the clearance within gas chamber 62 provided by protrusion 58 in annular side wall 22c may be an absolute value in a range from approximately 0.76 millimeters (0.030 inches) to approximately 1.54 millimeters (0.060 inches).

Figure 3C:
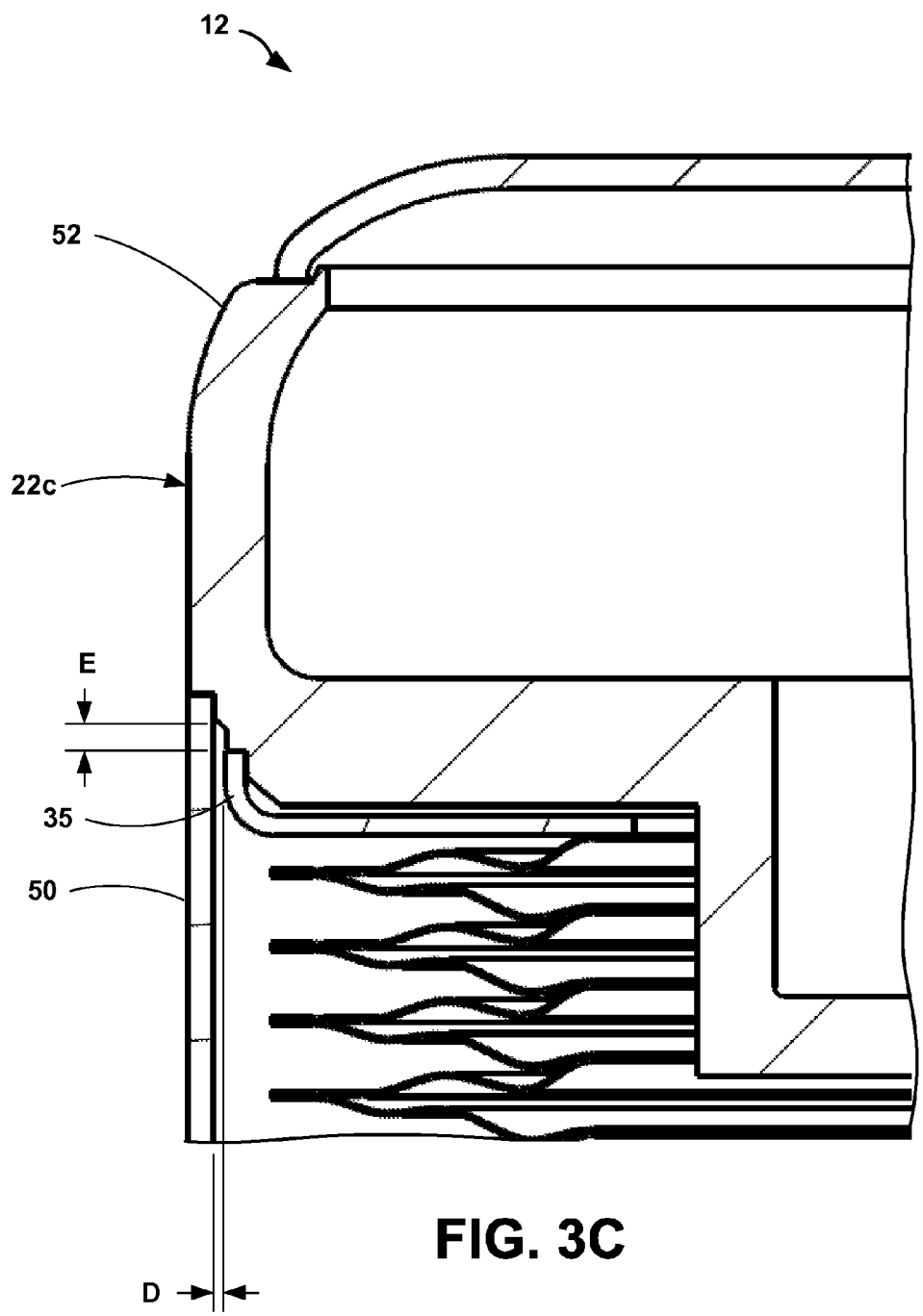

It should also be noted that while increasing the vertical distance E in FIG. 3C may accommodate the fluid connection between the pressure sensor and gas chamber 62, such change to IMD 12 may be impractical because it would effectively make the entire device larger, thereby increasing the footprint of the device within a patient as well as the cost to manufacture the device.

Figure 4:
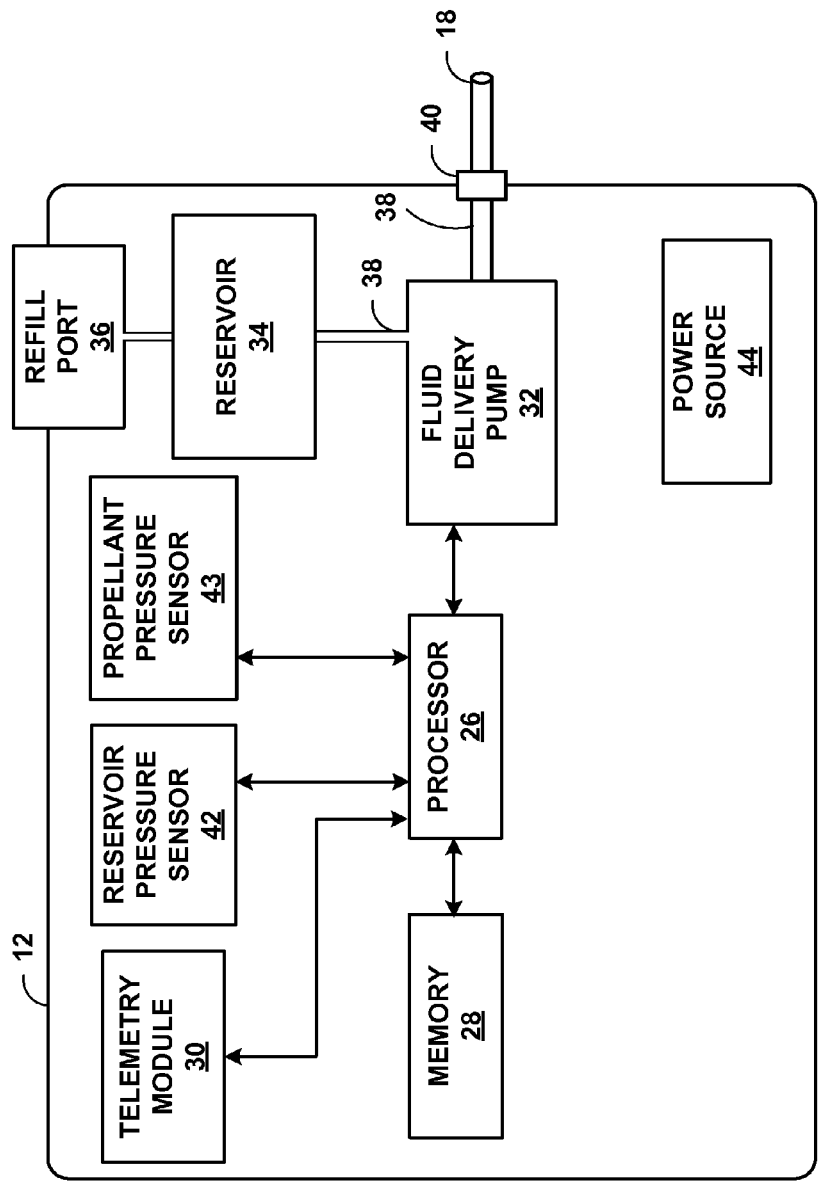
FIG. 4 is functional block diagram illustrating an example of the implantable fluid delivery device of FIG. 1.

FIG. 4 is a functional block diagram illustrating components of an example of IMD 12, which includes processor 26, memory 28, telemetry module 30, fluid delivery pump 32, reservoir 34, refill port 36, internal tubing 38, catheter access port 40, reservoir pressure sensor 42, propellant chamber pressure sensor 43, and power source 44. Processor 26 is communicatively connected to memory 28, telemetry module 30, and fluid delivery pump 32. Fluid delivery pump 32 is connected to reservoir 34 and internal tubing 38. Reservoir 34 is connected to refill port 36. Catheter access port 40 is connected to internal tubing 38 and catheter 18.

IMD 12 also includes power source 44, which is configured to deliver operating power to various components of the IMD. In some examples, IMD 12 may include a plurality of reservoirs for storing more than one type of therapeutic fluid. In some examples, IMD 12 may include a single long tube that contains the therapeutic fluid in place of a reservoir. However, for ease of description, an IMD 12 including a single reservoir 34 is primarily described with reference to the disclosed examples.

As described above, during operation of IMD 12, processor 26 controls fluid delivery pump 32 with the aid of instructions associated with program information that is stored in memory 28 to deliver a therapeutic fluid to patient 16 via catheter 18. Instructions executed by processor 26 may, for example, define therapy programs that specify the dose of therapeutic fluid that is delivered to a target tissue site within patient 16 from reservoir 30 via catheter 18. The programs may further specify a schedule of different therapeutic fluid rates and/or other parameters by which IMD 12 delivers therapy to patient 16.

In general, a therapy program stored on memory 28 and executed by processor 26 defines one or more therapeutic fluid doses to be delivered from reservoir 34 to patient 16 through catheter 18 by IMD 12. A dose of therapeutic fluid generally refers to a total amount of therapeutic fluid, e.g., measured in milligrams or other volumetric units, delivered over a total amount of time, e.g., per day or twenty-four hour period. The amount of therapeutic fluid in a dose may convey to a caregiver an indication of the probable efficacy of the fluid and the possibility of side effects.

In general, a sufficient amount of the fluid should be administered in order to have a desired therapeutic effect, such as pain relief. However, the amount of the therapeutic fluid delivered to the patient should be limited to a maximum amount, such as a maximum daily amount, in order not to avoid potential side effects. Therapy program parameters specified by a user, e.g., via programmer 20 may include fluid volume per dose, dose time period, maximum dose for a given time interval e.g., daily. In some examples, dosage may also prescribe particular concentrations of active ingredients in the therapeutic fluid delivered by IMD 12 to patient 16.

The manner in which a dose of therapeutic fluid is delivered to patient 16 by IMD 12 may also be defined in the therapy program. For example, processor 26 of IMD 12 may be programmed to deliver a dose of therapeutic fluid according to a schedule that defines different rates at which the fluid is to be delivered at different times during the dose period, e.g. a twenty-four hour period. The therapeutic fluid rate refers to the amount, e.g. in volume, of therapeutic fluid delivered over a unit period of time, which may change over the course of the day as IMD 12 delivers the dose of fluid to patient 16.

As an example, IMD 12 could be programmed to deliver therapeutic fluid to patient 16 at a rate of 20 microliters per hour. In the event the therapy program prescribes this fluid delivery rate for a twenty four hour period and assuming no patient or other boluses during the period of time, the dose of fluid delivered to patient 16 by IMD 12 will be 480 microliters (per twenty four hours). The therapy program may include other parameters, including, e.g., definitions of priming and patient boluses, as well as time intervals between successive patient boluses, sometimes referred to as lock-out intervals.

Therapy programs may be a part of a program group, where the group includes a number of therapy programs. Memory 28 of IMD 12 may store one or more therapy programs, as well as instructions defining the extent to which patient 16 may adjust therapy parameters, switch between therapy programs, or undertake other therapy adjustments. Patient 16 or a clinician may select and/or generate additional therapy programs for use by IMD 12, e.g., via external programmer 20 at any time during therapy or as designated by the clinician.

Components described as processors within IMD 12, external programmer 20, or any other device described in this disclosure may each include one or more processors, such as one or more microprocessors, digital signal processors (DSPs), application specific integrated circuits (ASICs), field programmable gate arrays (FPGAs), programmable logic circuitry, or the like, either alone or in any suitable combination.

In one example, processor 26 of IMD 12 is programmed to deliver a dose of therapeutic fluid to patient 16, which is defined in memory 28 of the device by a volume of therapeutic fluid delivered to the patient in one day. IMD 12 is also programmed according to a therapy schedule such that the fluid is delivered at different rates at different times during the day, which may be stored in memory 28, e.g., as a look-up table associating different fluid rates at different times during the day.

IMD 12 includes reservoir pressure sensor 42, which is configured to measure pressure in reservoir 34, and propellant gas chamber pressure sensor 43, which is configured to measure pressure in gas chamber 62 (see FIG. 3B). Reservoir pressure sensor 42 may be arranged in a number of locations within IMD 12 including, e.g., in reservoir 34 or refill port 26 or in bulkhead 52 with a fluid connection to the refill port and/or the reservoir. Pressure sensor 43 is arranged in bulkhead 52 adjacent protrusion 58 and is fluidly connected to propellant gas chamber 62 via fluid connection 64. Such pressure sensors as sensors 42 and 43 of IMD 12 may be employed in various therapeutic applications to estimate values related to the therapeutic fluid delivered by the device to patient 16. For example, processor 26 of IMD 12, alone or in conjunction with a processor of programmer 20 or another device communicatively connected to IMD 12, may be configured to measure the pressure of reservoir 34 and propellant gas chamber 40 and estimate the volume of therapeutic fluid in the reservoir based on a pressure differential between the reservoir pressure and the propellant gas chamber pressure. In addition to or in lieu of estimating therapeutic fluid volume within reservoir 34, processor 26 of IMD 12 may employ measurements from one or both of pressure sensors 42 and 43 to estimate a rate at which a fluid is added to or removed from the reservoir, e.g. during a refill operation. Examples of such techniques for estimating the volume of therapeutic fluid in a reservoir of an IMD and the rate at which a fluid is added to or removed from the reservoir are described in U.S. patent application Ser. No. 13/085,573, filed Apr. 13, 2011, and entitled "METHOD AND DEVICE FOR ESTIMATING VOLUME OF FLUID IN THERAPEUTIC FLUID DELIVERY DEVICE RESERVOIR."

Referring again to FIG. 4, memory 28 of IMD 12 stores program instructions and related data that, when executed by processor 26, cause IMD 12 and processor 26 to perform the functions attributed to them in this disclosure. For example, memory 28 of IMD 12 may store instructions for execution by processor 26 including, e.g., therapy programs, programs for monitoring the volume of therapeutic fluid in reservoir 34, and any other information regarding therapy delivered to patient 16 and/or the operation of IMD 12. Memory 28 may include separate memories for storing instructions, patient information, therapy parameters, therapy adjustment information, program histories, and other categories of information such as any other data that may benefit from separate physical memory modules. Therapy adjustment information may include information relating to timing, frequency, rates and amounts of patient boluses or other permitted patient modifications to therapy.

At various times during the operation of IMD 12 to treat patient 16, communication to and from IMD 12 may be necessary to, e.g., change therapy programs, adjust parameters within one or more programs, configure or adjust a particular bolus, or to otherwise download information to or from IMD 12. Processor 26 controls telemetry module 30 to wirelessly communicate between IMD 12 and other devices including, e.g. programmer 20. Telemetry module 30 in IMD 12, as well as telemetry modules in other devices described in this disclosure, such as programmer 20, can be configured to use RF communication techniques to wirelessly send and receive information to and from other devices respectively according to, e.g., the 802.11 or Bluetooth specification sets, infrared (IR) communication according to the IRDA specification set, or other standard or proprietary telemetry protocols. In addition, telemetry module 30 may communicate with programmer 20 via proximal inductive interaction between IMD 12 and the external programmer. Telemetry module 30 may send information to external programmer 20 on a continuous basis, at periodic intervals, or upon request from the programmer.

Power source 44 delivers operating power to various components of IMD 12. Power source 44 may include a small rechargeable or non-rechargeable battery and a power generation circuit to produce the operating power. In the case of a rechargeable battery, recharging may be accomplished through proximal inductive interaction between an external charger and an inductive charging coil within IMD 12. In some examples, power requirements may be small enough to allow IMD 12 to utilize patient motion and implement a kinetic energy-scavenging device to trickle charge a rechargeable battery. In other examples, traditional batteries may be used for a limited period of time. As another alternative, an external inductive power supply could transcutaneously power IMD 12 as needed or desired.

Figure 5:
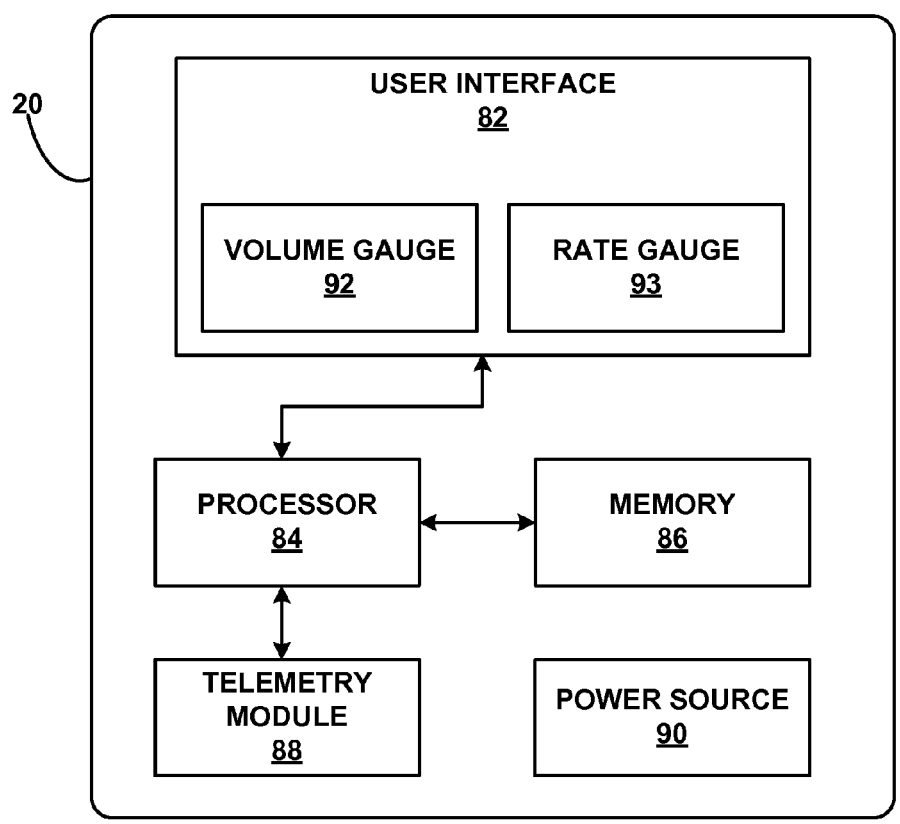
FIG. 5 is a functional block diagram illustrating an example of the external programmer of FIG. 1.

FIG. 5 is a functional block diagram illustrating an example of various components of external programmer 20 for IMD 12. As shown in FIG. 5, external programmer 20 may include user interface 82, processor 84, memory 86, telemetry module 88, and power source 90. A clinician or patient 16 interacts with user interface 82 in order to manually change the parameters of a therapy program, change therapy programs within a group of programs, view therapy information, view historical or establish new therapy programs, or otherwise communicate with IMD 12 or view or edit programming information. Processor 84 controls user interface 82, retrieves data from memory 86 and stores data within memory 86. Processor 84 also controls the transmission of data through telemetry module 88 to IMD 12. The transmitted data may include therapy program information specifying various therapeutic fluid delivery parameters. Memory 86 may store, e.g., operational instructions for processor 84 and data related to therapy for patient 16.

Programmer 20 may be a hand-held computing device that includes user interface 82 that can be used to provide input to programmer 20. For example, programmer 20 may include a display screen that presents information to the user and a keypad, buttons, a peripheral pointing device, touch screen, voice recognition, or another input mechanism that allows the user to navigate though the user interface of programmer 20 and provide input. In other examples, rather than being a handheld computing device or a dedicated computing device, programmer 20 may be a larger workstation or a separate application within another multi-function device.

User interface 82 may generally include a display screen or other output mechanisms and buttons or other input mechanisms that allow a user to receive information from and provide input to external programmer 20, respectively. In one example, user interface includes one or more of a touch pad, increase and decrease buttons, an emergency shut off button, and other buttons needed to control the therapy delivered to patient 16 by IMD 12. In another example, user interface 82 may additionally or only utilize a touch screen display including, e.g., a liquid crystal display (LCD), dot matrix display, organic light-emitting diode (OLED) display, touch screen, or any other device capable of delivering and/or accepting information. For visible indications of therapy program parameters or operational status, a display screen may suffice. For audible and/or tactile indications of therapy program parameters or operational status, programmer 20 may further include one or more audio speakers, voice synthesizer chips, piezoelectric buzzers, or the like.

User interface 82 may be configured to present therapy program information to the user as graphical bar graphs or charts, numerical spread sheets, or in any other manner in which information may be displayed. Further, user interface 82 may present nominal or suggested therapy parameters that the user may accept via user interface 82. User interface 82 also provides input mechanisms to enable the user to program IMD 12 in accordance with one or more therapy programs or otherwise provide data to IMD 12 necessary for delivering therapy to patient 16.

When programmer 20 is configured for use by a clinician, user interface 82 may be used to transmit initial programming information to IMD 12 including hardware information for system 10, e.g. the type of catheter 18, the position of catheter 18 within patient 16, a baseline orientation of at least a portion of IMD 12 relative to a reference point, and software information related to therapy delivery and operation of IMD 12, e.g. therapy parameters of therapy programs stored within IMD 12 or within programmer 20, the type and amount, e.g., by volume of therapeutic fluid(s) delivered by IMD 12 and any other information the clinician desires to program into IMD 12. The clinician may use programmer 20 during a programming session to define one or more therapy programs by which IMD 12 delivers therapy to patient 16, in which case patient 16 may provide feedback to the clinician during the programming session as to efficacy of a program being evaluated or desired modifications to the program. Programmer 20 may assist the clinician in the creation/identification of therapy programs by providing a methodical system of identifying potentially beneficial therapy parameters.

Programmer 20 may also be configured for use by patient 16. When configured as a patient programmer, programmer 20 may have limited functionality in order to prevent patient 16 from altering critical functions or applications that may be detrimental to patient 16. In this manner, programmer 20 may only allow patient 16 to adjust certain therapy parameters or set an available range for a particular therapy parameter. In some cases, a patient programmer may permit the patient to control IMD 12 to deliver a supplemental, patient bolus, if permitted by the applicable therapy program administered by the IMD, e.g., if delivery of a patient bolus would not violate a lockout interval or maximum dosage limit. Programmer 20 may also provide an indication to patient 16 when therapy is being delivered or when IMD 12 needs to be refilled or when the power source within programmer 20 or IMD 12 need to be replaced or recharged.

In one example, user interface 82 of programmer 20, whether employed as a patient or clinician programmer, may includes various text or graphical elements meant to convey information about the therapeutic fluid delivered by IMD to a user, e.g. patient 16 of a clinician. In one example, user interface 82 of programmer 20 may includes volume gauge 92 and/or rate gauge 93, which is configured to respectively indicate the volume of therapeutic fluid in reservoir 34 of IMD 12 and, under certain circumstances, the rate at which a fluid is added to or removed from the reservoir. Whether controlled by processor 26 of IMD 12, as described above, or processor 84 of programmer 20, volume gauge 92 may be configured to display via user interface 82 the volume of therapeutic fluid in reservoir 34 that is determined based on, e.g. the measured pressure differential between a pressure measured by reservoir pressure sensor 42 and a pressure measured by propellant chamber pressure sensor 43. Volume gauge 92 and/or rate gauge 93 included in user interface 82 may include any combination of text or graphical representations of the volume of fluid in reservoir 34.

Processor 84 of programmer 20 may be employed to execute any of a number of functions that may also be associated with processor 26 of IMD 12. For example, processor 84 of programmer 20 may be employed, in conjunction with or in lieu of processor 26 of IMD 12, to estimate the volume of therapeutic fluid in reservoir 34 based on, e.g., the measured pressure differential between a pressure measured by reservoir pressure sensor 42 and a pressure measured by propellant chamber pressure sensor 43 in a manner substantially similar to that described above with reference to processor 26 of IMD 12. For example, IMD 12 may transmit measurements of the pressure of reservoir 34 and propellant gas chamber 50 measured by reservoir pressure sensor 42 and gas chamber pressure sensor 43, respectively, to programmer 20 via telemetry modules 30 and 82 of IMD 12 and programmer 20, respectively. Processor 84 may then employ the measured pressures of reservoir 34 and propellant gas chamber 50 to estimate the volume of therapeutic fluid in the reservoir and/or the rate at which fluid is added to or removed from the reservoir, e.g. during a refill operation.

Telemetry module 88 allows the transfer of data to and from programmer 20 and IMD 12, as well as other devices, e.g. according to the RF communication techniques described above with reference to FIG. 2. Telemetry module 88 may communicate automatically with IMD 12 at a scheduled time or when the telemetry module detects the proximity of IMD 12. Alternatively, telemetry module 88 may communicate with IMD 12 when signaled by a user through user interface 82. To support RF communication, telemetry module 88 may include appropriate electronic components, such as amplifiers, filters, mixers, encoders, decoders, and the like. Programmer 20 may also communicate with another programmer or computing device via a wired or wireless connection using any of a variety of communication techniques, and/or via exchange of removable media, including, e.g., magnetic or optical disks, or memory cards or sticks including, e.g., non-volatile memory. Further, programmer 20 may communicate with IMD 12 or another device via, e.g., a local area network (LAN), wide area network (WAN), public switched telephone network (PSTN), or cellular telephone network, or any other terrestrial or satellite network appropriate for use with programmer 20 and IMD 12.

Power source 90 may be a rechargeable battery, such as a lithium ion or nickel metal hydride battery. Other rechargeable or conventional primary cell batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 12 in addition to programming IMD 12. Alternatively, a recharging device may be capable of communication with IMD 12. Then, the recharging device may be able to transfer programming information, data, or any other information described herein to IMD 12. In this manner, the recharging device may be able to act as an intermediary communication device between external programmer 20 and IMD 12.

The techniques described in this disclosure associated with control electronics of an IMD or external device, such as an external programmer may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Examples according to this disclosure provide techniques for arranging a pressure sensor and fluidly connecting the sensor to a propellant gas chamber of an IMD such that the sensor can measure the pressure within the chamber reliably and accurately. Examples according to this disclosure include IMD housings with a protrusion that is configured to provide clearance for a fluid connection between a propellant gas chamber pressure sensor and the gas chamber to enable the pressure sensor to reliably and accurately measure the pressure within the chamber. The protrusion enables reliable and repeatable fabrication of an IMD including a pressure sensor that can measure the pressure within the propellant gas chamber. Such measurements may be employed in various therapeutic applications to estimate, e.g., the volume of therapeutic fluid in a reservoir of an IMD, as well as the rate at which a fluid is added to or removed from the reservoir, e.g. during a refill operation.

Various examples have been described. These and other examples are within the scope of the following claims.

The invention claimed is:

1. An implantable fluid delivery device comprising:
   a reservoir configured to store a therapeutic fluid;
   a housing defining a chamber configured to at least partially surround the reservoir, wherein the chamber is configured to be filled with a propellant gas configured to regulate a pressure within the reservoir; and
   a pressure sensor configured to sense a pressure within the chamber,
   wherein the housing comprises a protrusion in an annular wall of the housing, the protrusion located at a first circumferential position in the annular wall and extending radially outward further from a central axis of the housing than a second circumferential position in the annular wall, wherein the first and second circumferential positions are in a common plane perpendicular to the central axis, wherein the protrusion is configured to provide clearance for fluid communication between the pressure sensor and the chamber.

2. The device of claim 1, wherein the housing comprises a shield defining the chamber at least partially surrounding the reservoir, wherein the shield comprises a circular first wall and at least a portion of the annular wall extending from the circular first wall, wherein at least a portion of the protrusion is formed in the portion of the annular wall of the shield.

3. The device of claim 2, wherein the housing comprises a bulkhead connected to the shield and configured to receive the pressure sensor.

4. The device of claim 3, further comprising a fluid connection between the pressure sensor and the chamber comprising a channel through the bulkhead from the pressure sensor to the protrusion in the portion of the annular wall of the shield.

5. The device of claim 3, further comprising a weld joint configured to create a hermetic seal between the bulkhead and the shield.

6. The device of claim 1, wherein the housing comprises two circular walls connected by the annular wall, and further comprising a header comprising a catheter junction to which a catheter is configured to be connected to the header, wherein the protrusion is formed in the annular wall circumferentially aligned with the catheter junction.

7. The device of claim 6, wherein the chamber is configured to surround the reservoir such that a periphery of the reservoir is offset from the annular wall of the housing by a first distance, and wherein the first distance between the periphery of the reservoir and the annular wall of the housing is constant around a circumference of the housing, except that the protrusion in the annular wall of the housing offsets the periphery of the reservoir from the annular wall by a second distance that is greater than the first distance.

8. The device of claim 7, wherein the second distance is 9 times larger than the first distance.

9. The device of claim 7, wherein the first distance is in a range from approximately 0.07 millimeters (0.00275 inches) to approximately 0.29 millimeters (0.0115 inches) and the second distance is in a range from approximately 0.76 millimeters (0.030 inches) to approximately 1.54 millimeters (0.060 inches).

10. The device of claim 7, wherein the second distance is defined as a function of a size of a fluid connection between the pressure sensor and the chamber.

11. The device of claim 10, wherein the fluid connection comprises a circular channel through a portion of the housing, and wherein the second distance is defined as a function of a diameter of the circular channel.

12. The device of claim 6, wherein the pressure sensor is connected to the housing adjacent the annular wall of the housing.

13. The device of claim 1, wherein the pressure sensor is connected to the housing adjacent a periphery of the housing.

14. The device of claim 1, further comprising a fluid connection comprising at least one of a channel in the housing or a tube connecting the pressure sensor to the chamber adjacent the protrusion.

15. An implantable fluid delivery device comprising:
a housing comprising two circular walls connected by an annular wall defining a chamber configured to at least partially surround a therapeutic fluid reservoir,
wherein the chamber is configured to be filled with a propellant gas configured to regulate a pressure within the therapeutic fluid reservoir, and
wherein the housing comprises a protrusion in the annular wall, the protrusion located at a first circumferential position in the annular wall and extending radially outward further from a central axis of the housing than a second circumferential position in the annular wall, wherein the first and second circumferential positions are in a common plane perpendicular to the central axis, and wherein the protrusion is configured to provide clearance for fluid communication between the chamber and a pressure sensor configured to sense a pressure within the chamber.

16. The device of claim 15, wherein the housing comprises a shield defining the chamber at least partially surrounding the therapeutic fluid reservoir, wherein the shield comprises one of the two circular walls and at least a portion of the annular wall extending from the one of the two circular walls, and wherein at least a portion of the protrusion is formed in the portion of the annular wall of the shield.

17. The device of claim 16, wherein the housing comprises a bulkhead connected to the shield and configured to receive the pressure sensor.

18. The device of claim 17, further comprising a fluid connection between the pressure sensor and the chamber comprising a channel through the bulkhead from the pressure sensor to the protrusion in the portion of the annular wall of the shield.

19. The device of claim 15, further comprising a header comprising a catheter junction to which a catheter is configured to be connected to the header, wherein the protrusion is formed in the annular wall circumferentially aligned with the catheter junction.

20. The device of claim 15, wherein the chamber is configured to surround the therapeutic fluid reservoir such that a periphery of the therapeutic fluid reservoir is offset from the annular wall of the housing by a first distance, and wherein the first distance between the periphery of the therapeutic fluid reservoir and the annular wall of the housing is constant around a circumference of the housing, except that the protrusion in the annular wall of the housing offsets the periphery of the therapeutic fluid reservoir from the annular wall by a second distance that is greater than the first distance.

21. The device of claim 15, further comprising a fluid connection comprising at least one of a channel in the housing or a tube connecting the pressure sensor to the chamber adjacent the protrusion.

22. An implantable fluid delivery system comprising:
a reservoir configured to store a therapeutic fluid delivered by an implantable fluid delivery device;
a housing defining a chamber configured to at least partially surround the reservoir, wherein the chamber is configured to be filled with a propellant gas configured to regulate a pressure within the reservoir;
a pressure sensor configured to sense a pressure within the chamber; and
means for providing clearance for fluid communication between the pressure sensor and the chamber via an extension of a first circumferential position in an annular wall of the housing radially outward further from a central axis of the housing than a second circumferential position in the annular wall, wherein the first and second circumferential positions are in a common plane perpendicular to the central axis.

* * * * *